United States Patent [19]

Bailey

[11] 4,420,000
[45] Dec. 13, 1983

[54] METHOD AND APPARATUS FOR MEASURING HEARTBEAT RATE

[75] Inventor: Wilber H. Bailey, Leucadia, Calif.

[73] Assignee: Camino Laboratories, Inc., San Diego, Calif.

[21] Appl. No.: 306,329

[22] Filed: Sep. 28, 1981

[51] Int. Cl.³ .............................................. A61B 5/04
[52] U.S. Cl. .................................................... 128/706
[58] Field of Search .............. 128/702, 703, 706, 687, 128/689, 690; 364/411, 413, 571, 572, 575, 737

[56] References Cited

U.S. PATENT DOCUMENTS

| | | | |
|---|---|---|---|
| 3,841,315 | 10/1974 | Kopp | 128/706 |
| 4,034,745 | 7/1977 | Bloom | 128/706 |
| 4,096,854 | 6/1978 | Perica et al. | 128/690 |
| 4,181,134 | 1/1980 | Mason et al. | 128/690 |
| 4,248,244 | 2/1981 | Charnitski et al. | 128/706 |
| 4,256,117 | 3/1981 | Perica et al. | 128/690 |
| 4,287,894 | 9/1981 | Lautenschläger et al. | 128/687 |

*Primary Examiner*—William E. Kamm
*Assistant Examiner*—Mitchell J. Shein
*Attorney, Agent, or Firm*—Fulwider, Patton, Rieber, Lee & Utecht

[57] ABSTRACT

A heart rate monitoring apparatus and related method for detecting the successive beats of a heart and providing a reliable estimate of heartbeat rate. The apparatus measures the time intervals between the successive beats and averages a prescribed number of the most recently occurring measurements. The particular measurement that differs most from the computed average is adjusted to be equal to that average, and the adjusted set of measurements is then averaged. These latter steps of adjusting and averaging are repeated a prescribed number of times, and the last-computed average is displayed as an estimate of heartbeat rate. The entire procedure is repeated upon the occurrence of each successive heartbeat.

24 Claims, 4 Drawing Figures

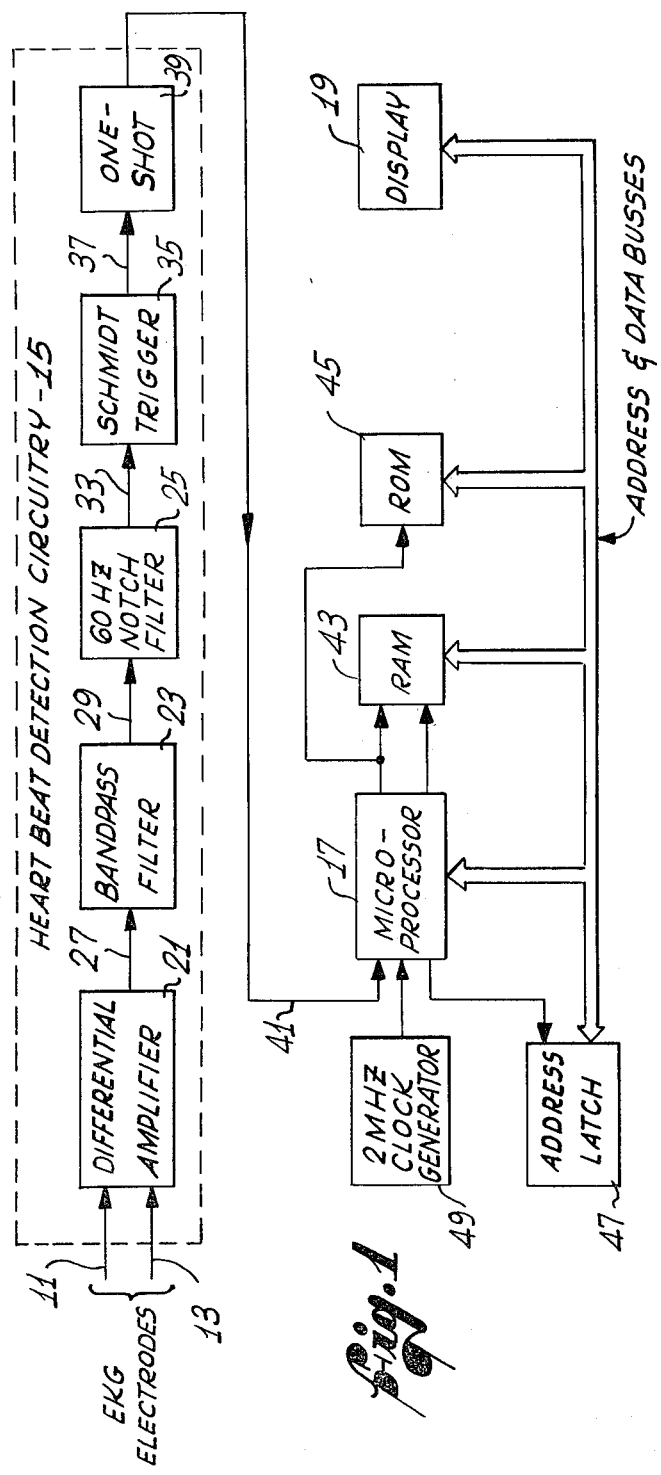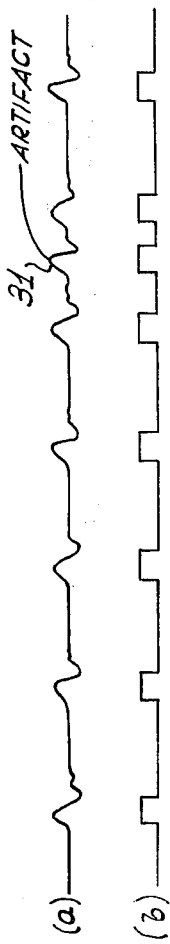

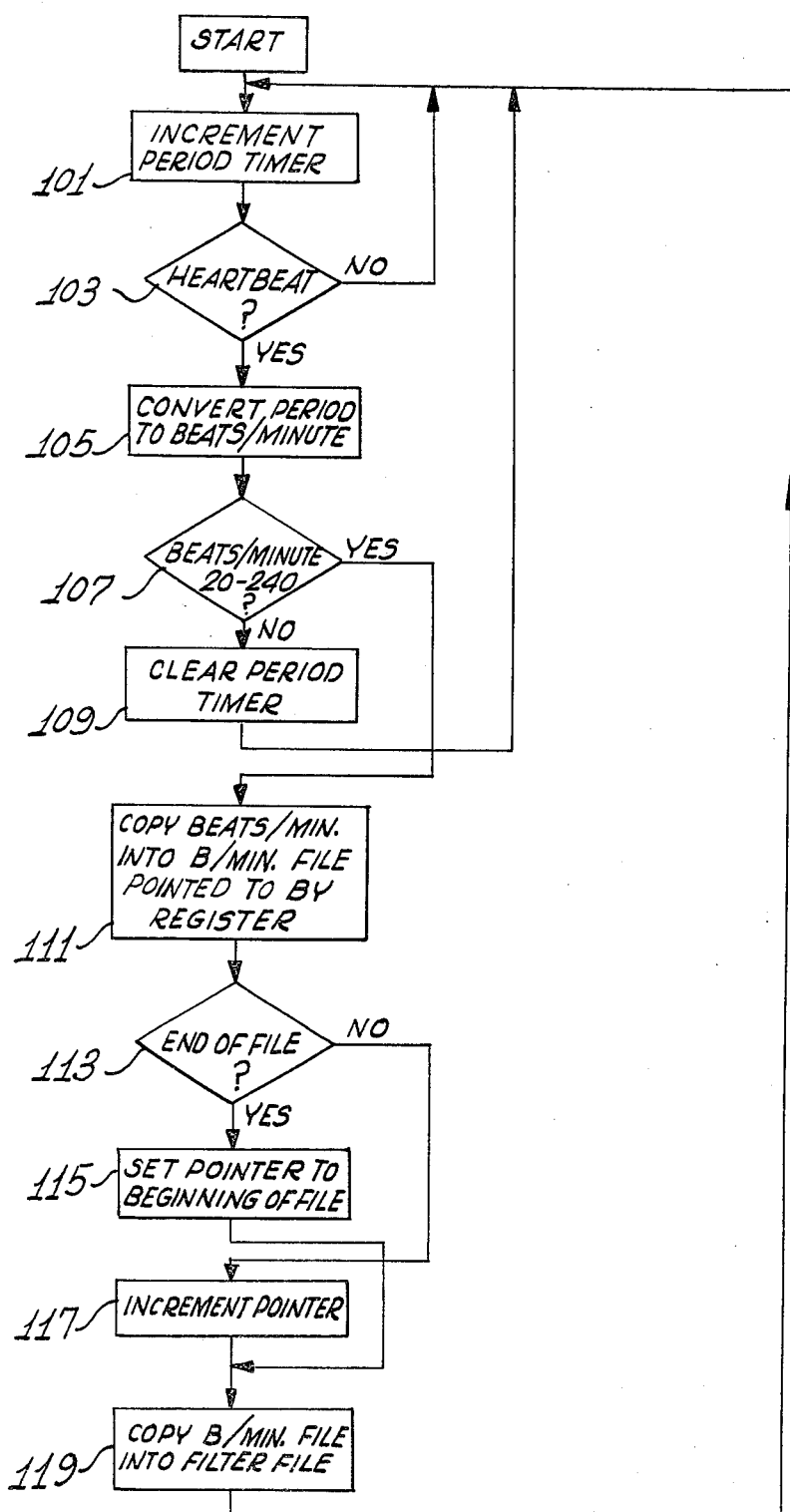

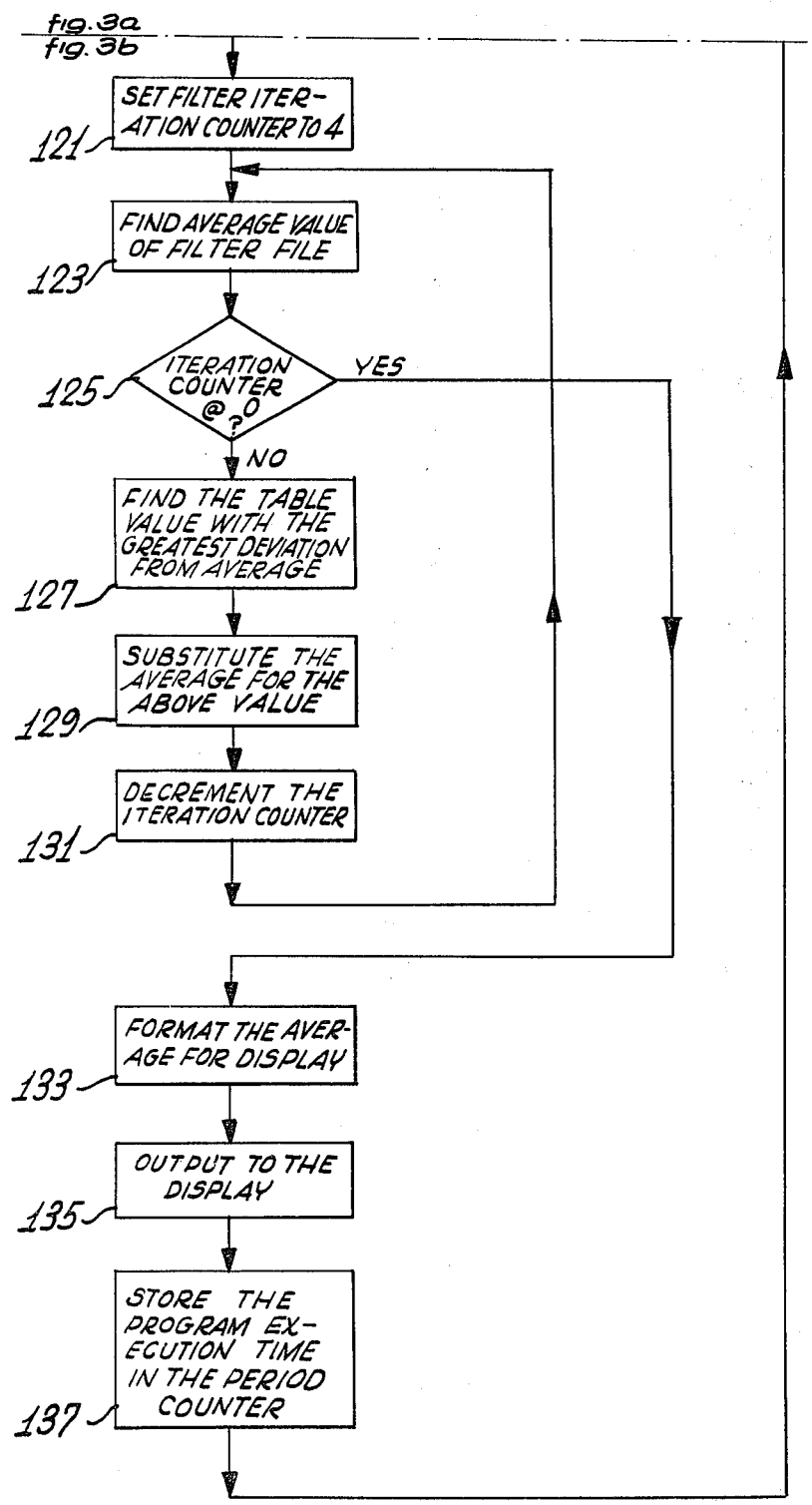

METHOD AND APPARATUS FOR MEASURING HEARTBEAT RATE

BACKGROUND OF THE INVENTION

This invention relates generally to heart rate monitors, and, more particularly, to heart rate monitors that adjust for heartbeat artifacts and thus provide more accurate estimates of heartbeat rate.

Heart rate monitors of this general type typically detect the successive heartbeats and measure the time durations between them. Each time duration measurement is converted into a corresponding frequency or rate, and a prescribed number of the most recently occurring measurements are averaged, to produce an estimate of the heartbeat rate. This estimate is updated upon the detection of each new heartbeat.

One drawback of the typical heart rate monitor described above is that heartbeat artifacts can sometimes cause inaccurate estimates of the heartbeat rate to be made. These artifacts can be caused, for example, by physical movement of electrode wires and by switching noise introduced through electrical power lines.

One solution to the problems associated with heartbeat artifacts is presented in U.S. Pat. No. 4,248,244 to Charnitski et al., in which detected beats are assumed to be artifacts if they occur at intervals differing from previous intervals by more than a prescribed percentage. These detected beats are discarded, and the timing for the next detected beat is reinitiated. Although this technique is generally effective in reducing the effects of heartbeat artifacts, it is not believed to be entirely satisfactory. This is because once a determination is made that a particular detected beat is an artifact, the timing information corresponding to it is discarded and thus not available for future use if it is later determined that the detected beat was in fact an actual heartbeat and not an artifact. Undue delay is then incurred before the apparatus once again provides an accurate estimate of heartbeat rate.

It should be appreciated from the foregoing that there is still a need for an effective heart rate monitor having means for reducing the effects of heartbeat artifacts, without introducing an undue time delay in providing an accurate estimate of heartbeat rate when an actual heartbeat is mistakenly assumed to be an artifact. The present invention fulfills this need.

SUMMARY OF THE INVENTION

The present invention is embodied in an apparatus and related method for monitoring the successive beats of a heart and for providing an accurate estimate of its current heartbeat rate, while reducing the effects of heartbeat artifacts. The apparatus includes means for measuring the time durations between the successive heartbeats and for producing a corresponding sequence of timing measurements, and means for averaging a prescribed set of the successive measurements, to produce a measurement average. In accordance with the invention, the apparatus further includes means for comparing each timing measurement in the set with the measurement average and adjusting a particular measurement in the set in accordance with the comparisons, thereby producing an adjustted set of timing measurements, and the means for averaging further operates to average the adjusted set, to produce an estimate of heartbeat rate. This adjustment is made whether or not a heartbeat artifact has occurred. When an artifact does occur, this technique substantially reduces its effect on the estimate of heartbeat rate.

In more detailed aspects of the invention, the prescribed set of timing measurements averaged by the averaging means corresponds to a prescribed number of the most recently occurring heartbeats. This set is therefore updated with the occurrence of each beat. Also, the particular measurement that is adjusted is the one that differs most from the measurement average. Further, the averaging means and the adjusting means operate repeatedly, a prescribed number of times, to average the adjusted set of timing measurements and to adjust the particular measurement in the set that differs most from the current adjusted measurement average. The final measurement average is output as the estimate of heartbeat rate.

In the preferred embodiment, the averaging means averages the timing measurements corresponding to the eight most recently occurring heartbeats, and the adjusting means successively operates four times to adjust the particular timing measurement that differs most from the corresponding measurement average. Also in the preferred embodiment, the adjusting means replaces the selected measurement with the last-computed measurement average. Thus, if a heartbeat artifact occurs, the timing measurements corresponding to it are adjusted several times in the direction of the actual heartbeat rate, so that the final estimate of heartbeat rate will correspond very closely with the actual rate.

In still another aspect of the invention, the sequence of timing measurements produced by the means for measuring corresponds to the rate or frequency of the corresponding detected heartbeats. In addition, the means for measuring further includes means for comparing each timing measurement to two prescribed thresholds, e.g., 20 bpm and 240 bpm. If the measurement is not intermediate the two thresholds, the measuring means assumes the measurement is caused by a heartbeat artifact, and the measurement is discarded.

Other aspects and advantages of the present invention should become apparent from the following description of the preferred embodiment, taken in conjunction with the accompanying drawings, which disclose, by way of example, the principles of the invention.

BRIEF DESCRIPTION OF THE DRAWINGS

FIG. 1 is a block diagram of a heartbeat monitor embodying the principles of the present invention;

FIG. 2 is a timing diagram showing the waveforms at two locations in the block diagram of FIG. 1; and FIGS. 3a and 3b together form a flowchart showing, in simplified form, the operational steps performed by the microprocessor of FIG. 1.

DESCRIPTION OF THE PREFERRED EMBODIMENT

Referring now to the drawings, and particularly to FIG. 1, there is shown an apparatus for detecting the successive beats of a heart and for producing a reliable estimate of heartbeat rate. The apparatus updates this estimate with each successive beat, and corrects for the incidence of heartbeat artifacts that would otherwise cause erroneous estimates to be made.

A pair of EKG electrodes (not shown) are attached to a person's skin and generate an electrical signal indicative of heartbeat activity. This signal is supplied to the apparatus over lines 11 and 13. The apparatus includes heartbeat detection circuitry 15 for detecting the successive beats and generating a corresponding pulse sequence signal (FIG. 2b), and a microprocessor 17 for measuring the time duration between the sequential pulses and converting each such measurement into a corresponding timing measurement indicative of heart rate. The microprocessor also processes the eight most recently occurring timing measurements in a prescribed fashion, to produce an estimate of heartbeat rate for display on a display device 19. This estimate is updated with the occurrence of each successive pulse.

In accordance with the invention, the microprocessor 17 produces the estimate of heartbeat rate by first averaging the eight timing measurements, then adjusting the particular one of the eight measurements that differs most from the average to be equal to that average, and finally computing an adjusted average based on the adjusted set of measurements. Further, these steps of adjusting and averaging are repeated four times, so that the final adjusted estimate of heartbeat rate is substantially unaffected by the occurrence of any heartbeat artifacts.

More particularly, the heartbeat detection circuitry 15 includes a differential amplifier 21 for amplifying the signal transmitted from the EKG electrodes and for converting it into single-ended form, and a bandpass filter 23 and a 60 Hz notch filter 25 for removing background noise. The single-ended EKG signal is coupled over line 27 from the differential amplifier to the bandpass filter, which limits the signal to a bandwidth between about 7 Hz and 25 Hz. This band-limited signal is, in turn, coupled over line 29 to the 60 Hz notch filter, which removes any 60 Hz noise that might have been picked up by the electrodes and electrode wires 11 and 13. The filtered EKG signal output by the notch filter (see FIG. 2a) includes a number of consecutive pulses caused by actual heartbeats, and additionally includes a heartbeat artifact 31 caused by some other source.

The filtered EKG signal is coupled over line 33 from the 60 Hz notch filter 25 to a Schmidt trigger 35, and in turn over line 37 to a monostable multivibrator or one-shot 39. These devices convert the filtered EKG signal into a pulse sequence signal, as shown in FIG. 2b. The duration of each pulse is preferably about 240 milliseconds.

The pulse sequence signal output by the heartbeat detection circuitry 15 is transmitted over line 41 to the microprocessor 17, which measures the time durations between the successive pulses and estimates the heartbeat rate. The preferred microprocessor is an RCA 1802 device, and it is associated with a random-access memory device (RAM) 43, a read-only memory device (ROM) 45, and an address latch device 47. Also associated with the microprocessor are a 2 MHz clock generator 49 for appropriately sequencing the microprocessor through its operations, and the display device 19 for providing a continuous display of the current estimate of heartbeat rate. These peripheral devices are interconnected with the microprocessor in a conventional manner, as taught in the User Manual published by RCA concerning the 1802 microprocessor. It will be understood by those of ordinary skill in the art that many other microprocessors, computers, or even hardware circuits might alternatively be used to implement the invention.

As previously mentioned, the microprocessor 17 and associated memory devices measure the time durations between the successive pulses of the pulse sequence signal and provide an estimate of heartbeat rate. Each time duration measurement is first converted to a corresponding rate, preferably expressed in beats per minute (bpm), and then stored in a file, taking the place of the earliest measurement previously stored. After a new measurement is entered into the file, the eight stored measurements are averaged, to produce an average rate measurement. The microprocessor then determines which of the eight measurements differs most from the average, and replaces that measurement with the average. These latter two steps of averaging and replacing are repeated three additional times, to provide a final estimate of heartbeat rate, which is continuously displayed until a new estimate is computed.

Referring now to FIGS. 3a and 3b, there is shown a flowchart implemented by the microprocessor 17 and associated devices of FIG. 1. Upon initiation of the apparatus, the microprocessor performs a first step 101 of incrementing a period timer used in measuring the time duration between successive pulses of the pulse sequence signal supplied on line 41. This timer is preferably incremented in steps of about two milliseconds. It is then determined at step 103 whether or not a pulse has occurred during the previous two milliseconds. If it has not, the program returns to the initial step of incrementing the period timer. If a heartbeat has occurred, on the other hand, step 105 converts the time duration measurement currently stored in the period timer to a corresponding heartbeat rate, preferably expressed in bpm.

After the heartbeat rate measurement is computed, step 107 determines whether or not the computed rate is intermediate prescribed thresholds of 20 bpm and 240 bpm. If it is not, it is assumed that the detected pulse was not in fact a heartbeat and the period timer is cleared at step 109. The program then returns to the initial step 101 of incrementing the period timer. If it is determined at step 107 that the computed rate measurement is intermediate the two thresholds of 20 bpm and 240 bpm, then step 111 copies that rate into a prescribed location of a bpm file. This file includes eight locations for rate measurements and the particular location in which each new rate measurement is placed is incremented in a cyclic fashion. The file thus always contains the rate measurements for the eight most recently occurring heartbeats.

After the rate measurement has been copied into its prescribed location in the bpm file, the program updates a pointer indicating the appropriate location for the next rate measurement to be copied. Specifically, it is determined at step 113 whether or not the eighth location in the file has been reached. If it has, step 115 sets the pointer to the first location in the file, whereas if it has not, step 117 increments the pointer by one unit.

After the pointer has been updated, step 110 copies the entire contents of the bpm file into a filter file, such that it, too, contains the rate measurements corresponding to the eight most recently occurring heartbeats. A filter iteration counter is then set to the number four at step 121, and the average value of the filter file is determined at step 123. Step 125 then determines whether or not the iteration counter is set to the number zero. If it is not, step 127 determines the particular entry in the filter table that differs most, arithmetically, from the average value determined in step 123. Step 129 substitutes this average value for the particular entry located in step 127. The iteration counter is then decremented by one unit at step 131 and the program returns to the averaging step 123, to determine the average value of the adjusted entries in the filter file.

The steps 123, 125, 127, 129, and 131 are repeated four times, until the step 125 determines that the iteration counter is set to the number zero. When this occurs, the last-computed average is appropriately formatted at step 133, and, in turn, output to the display device 19 at step 135. Finally, step 137 presets the program execution time into the period timer, and the program returns to the intial step 101. This program execution time should be a constant amount for each detected heartbeat, so the same number is preset into the period timer each time. Also, this execution time should be less than the minimum anticipated time duration between successive heartbeats, so that the programming steps outlined in FIG. 3 will be completed for each beat before the next succeeding beat occurs.

An example of the program's operation is provided in the table below. The eight entries in the Filter File 1 column indicate the heartbeat rates corresponding to each of the successive pulses of FIG. 2. The first five pulses and the last two pulses correspond to actual heartbeats, while the sixth pulse is caused by a heartbeat artifact 31. Thus, although the actual heartbeat rate is about 70 beats per minute, the presence of the artifact causes the sixth and seventh rate measurements to be 116 bpm and 175 bpm, respectively.

TABLE

| | FILTER FILE 1 | FILTER FILE 2 | FILTER FILE 3 | FILTER FILE 4 | FILTER FILE 5 |
|---|---|---|---|---|---|
| 1. | 70 bpm | 70 bpm | 70 bpm | 70 bpm | 70 bpm |
| 2. | 70 | 70 | 70 | 70 | 70 |
| 3. | 70 | 70 | 70 | 70 | 70 |
| 4. | 70 | 70 | 70 | 70 | 70 |
| 5. | 70 | 70 | 70 | 70 | 70 |
| 6. | 116 | 116* | 78 | 78* | 71 |
| 7. | 175* | 89 | 89* | 73 | 73 |
| 8. | 70 | 70 | 70 | 70 | 70 |
| Avg. | 89 bpm | 78 bpm | 73 bpm | 71 bpm | 71 bpm |

In accordance with the program's operation, the average value of the entries in the Filter File 1 is computed and determined to be about 89 bpm. Further, the apparatus determines that the seventh entry, indicated by the asterisk, differs by the most amount from the average value, so it replaces this entry with the average value to form the Filter File 2, shown in the second column of the Table. In the second iteration, the average value is determined to be 78 bpm and the sixth entry is determined to differ by the most amount from this average value. Accordingly, the sixth entry is adjusted to 78 bpm in forming the Filter File 3. This process is repeated two additional times, until the Filter File 5 is formed and its average computed. This average value, i.e., 71 bpm, is then displayed on the display device 19. Thus, in just four iterations, the initial estimate of 89 bpm is reduced to 71 bpm, which is substantially identical to the actual heartbeat rate of 70 bpm.

It should be appreciated from the foregoing description that the present invention provides an improved apparatus and method for detecting heartbeat activity and providing a reliable estimate of heartbeat rate. The apparatus averages the heartbeat rates for several consecutive heartbeats, and in addition corrects for the occurrence of heartbeat artifacts that otherwise might cause erroneous estimates of heartbeat rate to be made.

Although the present invention has been described in detail with reference to the presently-preferred embodiment, it should be understood by those of ordinary skill in the art that various modifications can be made without departing from the spirit and scope of the invention. Accordingly, the invention is not to be limited except as by the appended claims.

I claim:

1. A heart rate monitor comprising:
   detection means for measuring the time intervals between the successive beats of a heart and for producing a corresponding sequence of timing measurements;
   averaging means for averaging a prescribed set of the successive timing measurements, to produce a measurement average; and
   adjusting means for comparing each timing measurement in the set with the measurement average and adjusting a particular measurement in the set in accordance with the comparisons, thereby producing an adjusted set of timing measurements;
   wherein the means for averaging further operates to average the adjusted set of timing measurements, to produce an estimate of heartbeat rate.

2. A heart rate monitor as defined in claim 1, wherein the adjusting means including means to adjust the particular measurement in the set that differs most from the measurement average.

3. A heart rate monitor as defined in claim 2, wherein the adjusting means including means to adjust the particular measurement to equal the measurement average.

4. A heart rate monitor as defined in claim 1, wherein the averaging means including means to average the timing measurements corresponding to a prescribed number of the most recently occurring heartbeats, such that the prescribed set of timing measurements is updated upon the occurrence of each successive beat.

5. A heart rate monitor as defined in claim 4, including means for repeatedly operating said averaging means and said adjusting means a prescribed number of times, to average the adjusted set of timing measurements and produce an adjusted measurement average, and to adjust a prescribed measurement in the adjusted set of timing measurements, the final adjusted measurement average being the estimate of the heartbeat rate.

6. A heart rate monitor as defined in claim 5, wherein:
   the averaging means including means for averaging the timing measurements corresponding to about the eight most recently occurring heartbeats; and
   the adjusting means successively operates about four times to adjust the particular timing measurement that differs most from the corresponding measurement average.

7. A heart rate monitor as defined in claim 1, wherein the successive timing measurements produced by the detection means indicate the rate of the associated heartbeats, and
   wherein the detection means includes means for comparing each timing measurement to two prescribed thresholds, and for discarding the measurement if it is not intermediate to the two thresholds.

8. A heart rate monitor as defined in claim 1, wherein the detection means includes means for comparing each timing measurement to two prescribed thresholds, and for discarding the measurement if it is not intermediate the two thresholds.

9. A heart rate monitor comprising:
   means for measuring the time intervals between the successive beats of a heart and for producing a corresponding sequence of timing measurements;

means for averaging a prescribed number of the most recently occurring timing measurements to produce a measurement average, the prescribed set of timing measurements and the corresponding measurement average being updated upon the occurrence of each successive beat; and means for adjusting the particular measurement of the set that differs most from the measurement average to be equal to the measurement average, to produce an adjusted set of timing measurements;

wherein the means for averaging further operates to average the adjusted set of timing measurements and produce an estimate of heartbeat rate.

10. A heart rate monitor as defined in claim 9, including means for repeatedly operating said averaging means and said adjusting means, a prescribed number of times, to average the adjusted set of timing measurements and produce an adjusted measurement average, and to adjust the particular measurement in the adjusted set of measurements that differs most from the adjusted measurement average, the final adjusted measurement average being an estimate of heartbeat rate.

11. Apparatus for monitoring the beats of a heart and estimating heartbeat rate, comprising:

means for measuring the time intervals between the successive beats of a heart and for producing a corresponding sequence of timing measurements indicative of heartbeat rate, the means for measuring including means for comparing each timing measurement to prescribed upper and lower thresholds and for discarding the measurement if it is not intermediate the two thresholds;

means for averaging a prescribed number of the most recently occurring timing measurements to produce a measurement average, the prescribed set of timing measurements and the corresponding measurement average being updated upon the occurrence of each successive beat; and means for adjusting the particular measurement of the set that differs most from the measurement average to be equal to the measurement average, to produce an adjusted set of timing measurements;

wherein the means for averaging and the means for adjusting further operate repeatedly, a prescribed number of times, to average the adjusted set of timing measurements and produce an adjusted measurement average, and to adjust the particular measurement in the adjusted set that differs most from the adjusted measurement average, the final adjusted measurement average being an estimate of heartbeat rate.

12. A heart rate monitor as defined in claim 11, wherein:

the means for averaging including means for averaging the timing measurements corresponding to about the eight most recently occurring heartbeats; and the means for adjusting successively operates about four times to adjust the particular timing measurement that differs most from the corresponding measurement average.

13. A method for monitoring the beats of a heart and estimating heartbeat rate, comprising steps of:

measuring the time intervals between the successive heartbeats and producing a corresponding sequence of timing measurements;

averaging a prescribed set of the successive timing measurements, to produce a measurement average;

comparing each timing measurement in the set with the measurement average and adjusting the particular measurement in the set that differs most from the measurement average, thereby producing an adjusted set of timing measurements; and averaging the adjusted set of timing measurements to produce an estimate of heartbeat rate.

14. A method as defined in claim 13, wherein the step of comparing and adjusting adjusts the particular measurement to equal the measurement average.

15. A method as defined in claim 13, wherein the first step of averaging averages the timing measurements corresponding to a prescribed number of the most recently occurring heartbeats, such that the prescribed set of timing measurements is updated upon the occurrence of each successive beat.

16. A method as defined in claim 15, wherein the second step of averaging and the step of comparing and adjusting are repeated a prescribed number of times, to average the adjusted set of timing measurements and produce an adjusted measurement average, and to adjust a prescribed measurement in the adjusted set, the final adjusted measurement average being the estimate of the heartbeat rate.

17. A method as defined in claim 16, wherein:

the first step of averaging averages the timing measurements corresponding to the eight most recently occurring heartbeats; and the step of comparing and adjusting is performed successively four times to adjust the particular timing measurement that differs most from the corresponding measurement average.

18. A method as defined in claim 13, wherein the successive timing measurements produced in the step of measuring indicate the rate of the associated heartbeats.

19. A method as defined in claim 13, wherein the step of measuring includes steps of:

comparing each timing measurement to two prescribed thresholds; and discarding the measurement if it is not intermediate the two thresholds.

20. A method for monitoring the beats of a heart and estimating heartbeat rate, comprising steps of:

measuring the time intervals between the successive heartbeats and producing a corresponding sequence of timing measurements;

averaging a prescribed number of the most recently occurring timing measurements, to produce a measurement average;

adjusting the particular measurement in the set that differs most from the measurement average to be equal to the measurement average, to produce an adjusted set of timing measurements; and averaging the adjusted set of timing measurements, to produce an estimate of heartbeat rate.

21. A method as defined in claim 20, and further including a step of repeating the step of adjusting and the second step of averaging a prescribed number of times, the final repeated step of averaging producing the estimate of heartbeat rate.

22. A heart rate monitor comprising:

means for measuring the time intervals between the successive beats of a heart and for producing a corresponding sequence of timing measurements;

means for grouping the timing measurements into a prescribed set and adjusting a particular measurement of the set in a prescribed fashion, to produce an adjusted set of timing measurements; and means for averaging the adjusted set of timing measurements, to produce an estimate of heartbeat rate.

23. A heart rate monitor as defined in claim 22, wherein:

said means for grouping includes means for updating the set of measurements;

on the occurrence of each successive beat; and the means for grouping including means to adjust the particular measurement of the set that differs most from the measurement average to be equal to the measurement average.

24. A heart rate monitor as defined in claim 23, including means for repeatedly operating said averaging means and said adjusting means, a prescribed number of times, to average the adjusted set of timing measurements and produce an adjusted measurement average, and to adjust a prescribed measurement in the adjusted set of timing measurements, the final adjusted measurement average being the estimate of the heartbeat rate.

* * * * *